United States Patent [19]

Croce

[11] Patent Number: 5,149,628

[45] Date of Patent: Sep. 22, 1992

[54] METHODS FOR DETECTING BCL-3 GENE IN HUMAN LEUKEMIAS

[75] Inventor: Carlo M. Croce, Philadelphia, Pa.

[73] Assignee: Temple University, Philadelphia, Pa.

[21] Appl. No.: 436,888

[22] Filed: Nov. 15, 1989

[51] Int. Cl.$^5$ .................. C12Q 1/68; C12Q 15/00; G01N 33/566; C07H 15/12

[52] U.S. Cl. ........................... 435/6; 435/5; 435/7.23; 435/122.3; 436/501; 436/538; 436/813; 536/27; 935/19; 935/2

[58] Field of Search ............ 435/6, 69.1, 252.33, 435/7.23; 436/538, 813; 536/27; 935/19, 24, 78

[56] References Cited

U.S. PATENT DOCUMENTS 4,857,466  8/1989  Saunders et al. ............ 435/252.33

OTHER PUBLICATIONS

Dayton et al. P.N.A.S. 81: 4495–99 (1984).
Sheldon et al. P.N.A.S. 85:3052–56 (1988).
Ohno et al. Cell 60: 991–97 (1990).
Gauwerky et al. P.N.A.S. 86:8867–71 (1989).
Lewin, "Genes", third edition, John Wiley & Sons, 1987, p. 709.
Gauwerky, et al., Proc. Natl. Acad. Sci. USA, vol. 85, pp. 8548–8552 (1988).
ar-Rushdi et al., "Differential Expression of the Translocated and the Untranslocated c-myc Oncogene in Burkitt Lymphoma," Science (1983), 222: 390–393.
Payvar et al., "Sequence-Specific Binding of Glucocorticoid Receptor to MTV DNA at Sites within and Upstream of the Transcribed Region," Cell (1983), 35: 381–392.
Slamon et al., "Expression of Cellular Oncogenes in Human Malignancies," Science (1984), 224: 256–262.
Gidoni et al., "Multiple Specific Contacts Between a Mammalian Transcription Factor and Its Cognate Promoters," Nature (1984), 312: 409–413.
Tsujimoto et al., "The t(14;18) Chromosome Translocations Involved in B-Cell Neoplasms Result from Mistakes in VDJ Joining," Science (1985), 229: 1390–1393.
Haluska et al., "Oncogene Activation by Chromosome Translocation in Human Malignancy," Ann. Rev. Genet. (1987), 21: 321–345.
Levine et al., "Cytogenetic Abnormalities Predict Clinical Outcome in Non-Hodgkin Lymphoma," Ann. Intern. Med. (1988), 108: 14–20.
Bhandari et al., "Cloning, Nucleotide Sequence, and Potential Regulatory Elements of the Glutamine Synthetase Gene from Murine 3T3-L1 Adipocytes," Proc. Natl. Acad. Sci. USA (1988), 85: 5789–5793.
Schule et al., "Many Transcription Factor Interact Synergistically with Steroid Receptors," Science (1988), 242: 1418–1420.
Schule et al., "Cooperativity of the Glucocorticoid Receptor and the CACCC-box Binding Factor," Nature (1988), 332: 87–90.
Nowell, "Molecular Events in Tumor Development," New Eng. J. Medicine (1988), 319: 575–577.
DeJong et al., "Activation of the c-myc Oncogene in A Precursor B-Cell Blast Crisis of Follicular Lymphoma, Presenting as Composite Lymphoma," New. Eng. J. Med. (1988), 318: 1373–1378.

Primary Examiner—Robert A. Wax
Assistant Examiner—Miguel H. Escallon
Attorney, Agent, or Firm—Banner, Birch, McKie & Beckett

[57] ABSTRACT

Bcl-3 gene sequences can be used to monitor the success of chemotherapy and to detect minimal residual disease in patients having hematopoietic malignancies. Bcl-3 sequences can also be used to identify new cellular oncogenes involved in hematopoietic cell malignancies by taking advantage of their adjacency to the bcl-3 promoter. Particular nucleic acid probes and primers are also provided by the disclosure.

13 Claims, 7 Drawing Sheets

METHODS FOR DETECTING BCL-3 GENE IN HUMAN LEUKEMIAS

The U.S. Government has paid-up license in this invention and the right in limited circumstances to require the patent owner to license others on reasonable terms as provided for by the terms of Grant Nos. CA 01279 and CA 39860 from the National Institutes of Health.

TECHNICAL FIELD OF THE INVENTION

The invention relates to the field of cancer diagnostics. More particularly, it relates to diagnosis of cancers of the hematopoietic lineages, such as B-cell, T-cell and non-B, non-T leukemias.

BACKGROUND OF THE INVENTION

Activation of the cellular oncogene c-myc is associated with highly aggressive tumors. For example, in Burkitt lymphoma the oncogene is activated by a t(8;14) translocation. (Ar-Rushdi et al., Science, vol. 222, pp. 390-393, 1983). In addition, c-myc activation has been shown to be associated with the progression of a low grade B-cell lymphoma to a high grade B-cell malignancy. (Gauwerky, et al. Oncogene, vol. 2, pp. 431-435, 1988; and Proc. Natl. Acad. Sci., vol. 85, pp. 8548-8552, 1988.) During the progression of the malignancy, a t(8;14) translocation is acquired which activates the c-myc gene. Translocation causes activation of c-myc by juxtaposing it to the immunoglobulin heavy-chain locus (IgH). (Klein, et al., 1985, Nature, vol. 315, pp. 190-195.)

Other cellular oncogenes have been found whose expression is altered upon translocation. See, Haluska, Ann. Rev. Genet. vol. 21, pp. 321-345, 1989. In addition, other genes have been found which activate oncogenes upon translocation, e.g., the T-cell receptor loci, as well as the Ig light chain loci.

Knowledge of the molecular basis of various cancers, such as the particular genes involved in the translocations, renders accurate diagnosis and monitoring of the cancers possible. Thus, there is a continuing need in the art for identification and isolation of additional genes involved in oncogenic processes.

SUMMARY OF THE INVENTION

It is an object of the invention to provide a DNA probe for detecting rearrangements involving the bcl-3 locus.

It is another object of the invention to provide a method for detecting human hematopoietic cell neoplasms.

It is yet another object of the invention to provide a method of identifying new cellular oncogenes.

It is still another object of the invention to provide a method of monitoring the progress of anti-neoplastic therapy in a patient with a hematopoietic malignancy or of detecting minimal residual disease.

These and other objects of the invention are provided by one or more of the embodiments described below. In one embodiment a nucleic acid probe is provided which comprises a segment of the bcl-3 locus.

In another embodiment a method of detecting human hematopoietic cell malignancies is provided which comprises isolating nucleic acids from blood cells or bone marrow cells of a human; and determining whether in the nucleic acids isolated from said cells a bcl-3 gene is adjacent to sequences different from those to which bcl-3 is adjacent in germline sequences, the presence of different sequences adjacent to bcl-3 indicating a hematopoietic cell neoplasm.

In yet another embodiment of the invention a method of identifying cellular oncogenes is provided which comprises isolating nucleic acids from blood or bone marrow cells of humans having a hematopoietic cell neoplasm; and determining whether a gene other than bcl-3 is under the transcriptional control of a bcl-3 promoter in the nucleic acids isolated from said cells, a gene other than bcl-3 under the control of the bcl-3 promoter indicating that the gene is a cellular oncogene.

In still another embodiment of the invention a method of monitoring the progress of anti-neoplastic therapy in a patient with a hematopoietic cell malignancy or of detecting minimal residual disease is provided which comprises isolating nucleic acids from blood or bone marrow cells of a patient with a hematopoietic cell malignancy, wherein there is a rearranged bcl-3 gene in malignant cells of said patient; and determining whether the rearranged bcl-3 gene is present in the nucleic acids isolated from said blood or bone marrow cells, the presence of a rearranged bcl-3 gene indicating the presence of malignant cells in the patient.

The present invention thus provides the art with new diagnostic methods for certain hematopoietic cell malignancies as well as tools for locating new oncogenes which become associated with the bcl-3 locus during the neoplastic process.

BRIEF DESCRIPTION OF THE DRAWINGS

FIG. 3 (A) provides a restriction map analysis of the recombinant clones lambda 7B-1 and lambda 1A-1 involved in the t(14;18) translocation on chromosomes 14q+ and 18q−. Clone lambda 6B-5 represents a stretch of the germline bcl-2 gene that is derived from the normal chromosome 18. The horizontal lines represent DNA inserted into EMBL3A lambda phage. The bold line indicates the portion that is derived from the immunoglobulin heavy chain gene on chromosome 14. The triangle shows the breakpoints.

FIG. 4 depicts the nucleotide sequence across the breakpoint involving c-myc. The sequence from the patient with the rearranged bcl-3 gene is shown in the upper line and is compared to a sequence of the normal, germline c-myc gene. The bracket indicates the 3' end of the c-myc exon 1. The triangle designates the breakpoint on the exon 1. DNA binding sites such as a CACC box, a heptamer having similarity to the glucocorticoid response element (underlined), and an Sp1 binding site (CCGCCC) are indicated. DNA sequences were obtained using the Sanger dideoxy chain termination method on the M13 subclone mp11A-1-1; 1.7 from the SstI site on exon 1 of c-myc (see FIG. 3B).

FIG. 5 tabulates the presence of the probe p11A-1-1; 5.6 in a panel of 15 rodent-human hybrids; ▬ indicates that the hybrid named in the left column contains the chromosome indicated in the upper row; ▭ indicates presence of the long arm (or part of the long arm, indicated by a smaller fraction of stippling) of the chromosome shown above the column; ▭ indicates presence of the short arm (or partial short arm) of the chromosome listed above the column; and ▭ indicates the absence of the chromosome listed above the column. The column for chromosome 17 is boldly outlined and stippled to highlight correlation of presence of this chromosome (or region of this chromosome) with the presence of the respective probe. The patterns of retention of the probe p11A-1-1; 5.6 in the panel of hybrids is shown in the column to the right of the figure, where presence of the probe in the hybrid is indicated by a stippled box with a plus (+) sign and absence of the probe is indicated by an open box enclosing a minus (−) sign.

FIG. 6 shows how the gene for p11A-1-1; 5.6 was localized in the human genome by chromosomal in situ hybridization. The distribution of 145 grains on 75 spreads was scored.

DETAILED DESCRIPTION OF THE INVENTION

It is a discovery of the present invention that a newly identified gene, bcl-3, located on chromosome 17, band q22 is involved in the oncogenic process. This gene is expressed in all cells tested of the hematopoietic lineage but not in other types of cells. When the known cellular oncogene c-myc is translocated to a position adjacent to the bcl-3 promoter, c-myc expression is deregulated. Deregulation of c-myc is thought to cause aggressive neoplastic growth. One particular translocation studied involving bcl-3 and c-myc, t(8;17), which was cytogenetically undetectable, was found in a case of a very aggressive acute prolymphocytic leukemia.

Figure 3C:
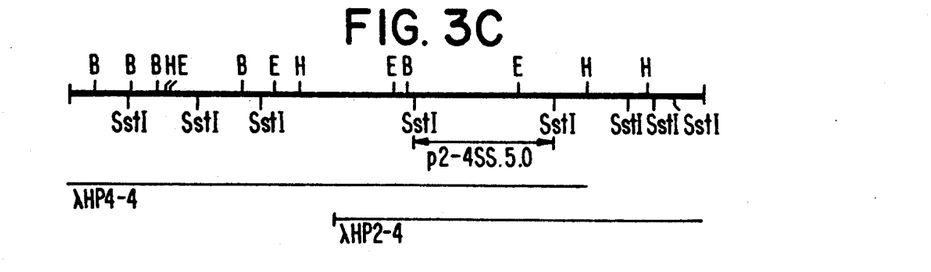
FIG. 3C provides a restriction map analysis of the recombinant clones lambda HP2-4 and lambda HP4-4 derived from a human placenta library. They represent the normal chromosome 17 encompassing the portion of the breakpoint. Cleavage sites of the restriction enzymes: B=BamHI, E=EcoRI, H=HindIII, Sma=SmaI X=?, RI=?. Scale bar, 2 kb.
Figure 4:
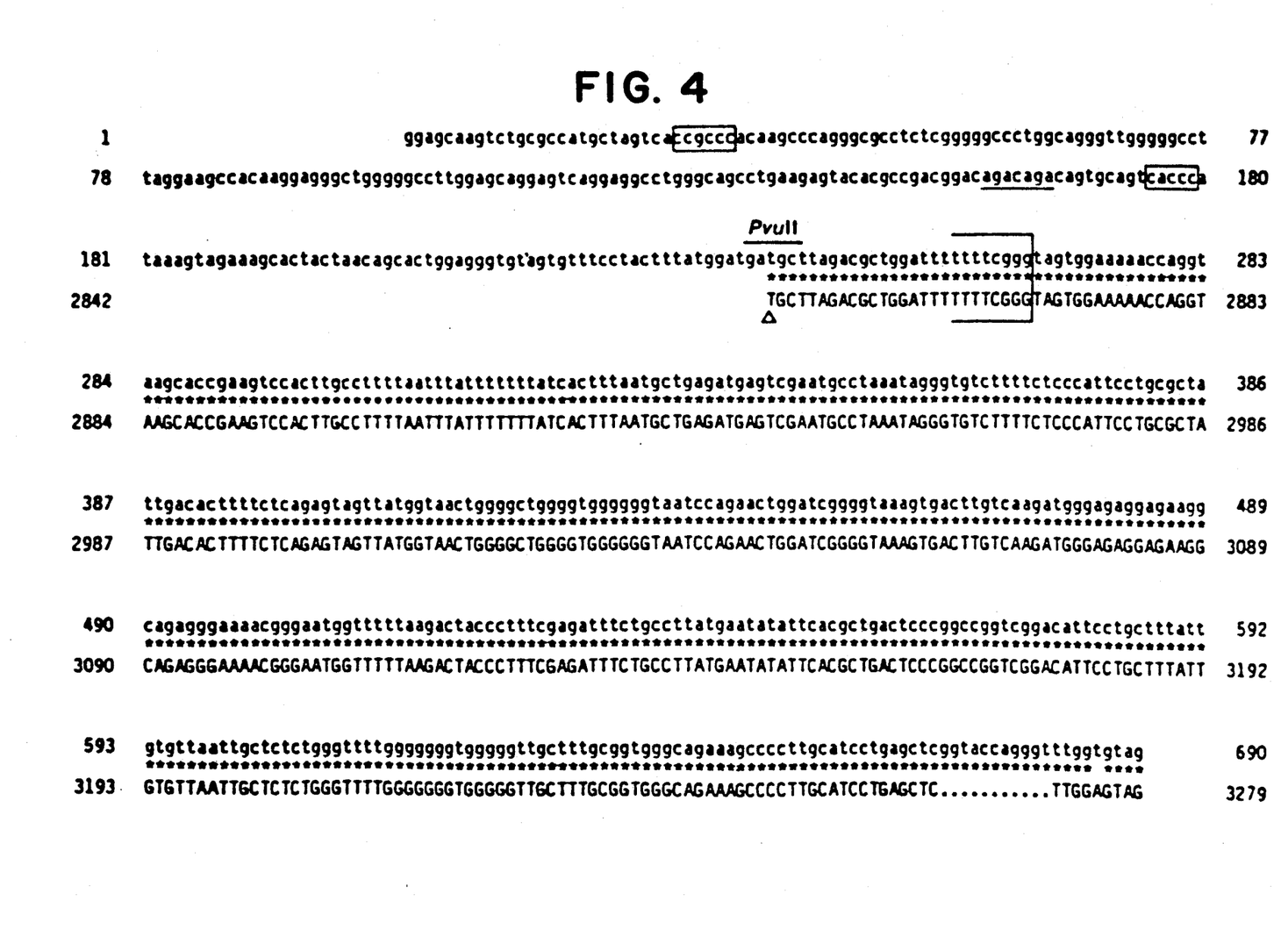

The nucleotide sequence of the promoter region of bcl-3 is shown in FIG. 4 as nucleotides number 1 to about 240. It displays a number of interesting features including a binding site for human transcription factor Sp1, (see, Gidoni, et al., Nature, vol. 312, pp. 409–412, 1984,) GC-rich repeat units, a sequence with similarility to a glucocorticoid response element, (see, Payvan, et al., Cell, vol. 35, pp. 381–392, 1983, and Bhandaro, et al., Proc. Natl., Acad. Sci., USA, vol. 85, pp. 5789–5793, 1988,) and a CACCC box (see, Dierks, et al., Cell, vol. 32, pp. 695–706, 1983). The promoter region of the bcl-3 gene is carried on three molecular clones shown in FIG. 3C, p2-4.SS.5.0, lambda HP4-4, and lambda HP2-4. All three clones span the breakpoint formed by the t(8;17) translocation.

According to the present invention a nucleic acid probe is provided. The probe comprises a segment of the bcl-3 locus. A nucleic acid probe according the invention may be either ribonucleic acid or deoxyribonucleic acid. The probe may also contain derivatives of the normal nucleic acid nucleotides such as radiolabelled nucleotides or fluorescent-labelled nucleotides. A nucleic acid probe, as used in the art, is used for detection of particular sequences of nucleotides by means of hybridization. The hybridization is based on complementarity such that similar or identical sequences are identified by a probe by means of the hybridization of a strand of the probe to a strand of the test nucleic acid. Such hybridization techniques are well-known in the art. One particularly useful technique is that of Southern, in which a test sample of DNA is digested with a restriction endonuclease and separated on an electrophoretic gel matrix. The separated DNA fragments are transferred to a filter such that the nucleic acid fragments retain the pattern of separation which was obtained on the electrophoretic gel matrix. The nucleic acids on the filter are then denatured to separate the strands and mixed with the nucleic acid probe to obtain hybrids between the probe and complementary sequences on the filter. Hybrids may be detected by means of a label attached to the probe such as a radiolabel or a fluorescent label.

A probe will generally be of a length sufficient to hybridize to its corresponding identical sequence without adventitiously binding to a number of unrelated sequences. Such length is generally greater than about 12 nucleotides and preferably greater than about 20 nucleotides. Probes of much greater length can also be used as is convenient. The probe will comprise a segment of the bcl-3 locus. The nucleic acid probe may consist of a bacterial plasmid, a viral vector, or other vector, or may consist of an isolated piece of nucleic acid. One means of isolating such a nucleic acid probe is by employing the DNA samples deposited at the American Type Culture Collection, Rockville, Md., (ATCC). Two bacterial phages and one plasmid were deposited which comprise all or part of the bcl-3 locus. These consist of p11A-1-1;5.6 (ATCC #40701), lambda HP2-4 (ATCC #40700), and lambda HP4-4 (ATCC #40702). See FIG. 3. The term bcl-3 locus refers to the entire gene whose promoter is contained on the three molecular clones deposited. The promoter sequence of the bcl-3 gene is shown in FIG. 4 between nucleotides numbered 1-240. Whereas the entire gene may not be contained on any of the three deposited molecular clones, the rest of the gene can easily be obtained using techniques known in the art, such as the well-known "chromosome walking" technique.

Nucleic acid primers are also provided by the present invention. These are generally single stranded molecules of nucleic acid which can be used in the polymerase chain reaction (see, U.S. Pat. Nos. 4,683,195; 4,683,202; 4,683,194, incorporated by reference herein) in order to amplify particular sequences located between the two primers used. According to the present invention these primers are derived from sequences in bcl-3 and in myc locus. When these primers are used to amplify sequences from DNA isolated from patients, an amplified product of a particular size is expected for a bcl-3/myc rearrangement.

The present invention also provides a method of detecting human hematopoietic cell neoplasms. Such neoplasms comprise B-cell or T-cell neoplasms including leukemias and lymphomas. In addition, detection of non T-, non B-cell leukemias are also encompassed by the method of the present invention. The neoplasms may also be tumors of histiocytes, i.e., those that have arisen from macrophages or from null cells or from progenitor cells. According to any of the methods of the present invention, DNA is first isolated from either peripheral blood cells or bone marrow cells of a human. Means of obtaining such cells and isolating DNA therefrom are well-known in the art and need not be elaborated here. Generally, cells will be broken open and the DNA separated from other components of the cell such as the membranes and proteins.

According to one method of the present invention hematopoietic cell neoplasms can be detected in humans. In order to do so, DNA is isolated from blood cells or bone marrow cells of a human as described above. The isolated DNA is examined to determine whether the bcl-3 locus is adjacent to sequences different from those to which bcl-3 is adjacent in germline DNA. If different sequences are present adjacent to the bcl-3 locus than are present in the germline sequences, a hematopoietic cell neoplasm is indicated. Determining which sequences are adjacent to the bcl-3 locus can be accomplished by any means known in the art. According to one means a nucleic acid probe containing bcl-3 sequences is hybridized to the isolated DNA. Generally the DNA will have been digested with a restriction endonuclease prior to hybridization. If a DNA fragment is found hybridizing to the bcl-3 probe which is different in size or composition from that found when DNA isolated from germline cells are used, then it is indicative of a rearrangement in the bcl-3 locus. Further, such a rearrangement is indicative of a hematopoietic cell neoplasm. Germline DNA sequences can be obtained, for example, from placenta, or other tissues which are known in the art.

According to another means for determining whether the bcl-3 locus is adjacent to germline or non-germline sequences, bcl-3 sequences present in the DNA isolated from blood or bone marrow cells are amplified. The amplification is done using the well-known polymerase chain reaction (see references above). Nucleic acid primers (as described above) are used to initiate the reaction. If amplification products are found, a rearrangement of the bcl-3 gene with the myc gene is indicated. This implies the presence of a t(8;17) chromosome translocation.

In another method of the present invention, new cellular oncogenes can be identified using the bcl-3 gene sequences. As bcl-3 has been shown to activate the c-myc oncogene, the activated oncogene is known to be involved in aggressive tumors, and the bcl-3-c-myc gene fusion was found in a sample from a patient with an extremely aggressive malignancy, it is likely that in other malignancies the bcl-3 gene activates other cellular oncogenes. Although many oncogenes are known, (see Haluska, Annual Rev. Genet. 1987, vol. 21, pp. 321-345 for a review) many malignancies are known for which no change in the known cellular oncogenes has been found. Thus it is likely that other cellular oncogenes are involved in these cancers.

In order to locate and identify new cellular oncogenes, DNA can be isolated from blood or bone marrow cells of humans having a hematopoietic cell neoplasm. Obtaining such cells and DNA can be performed as described above. Then, using the DNA from the humans having neoplasms, the bcl-3 locus is analyzed to determine whether a gene other than the bcl-3 gene is under the transcriptional control of the bcl-3 promoter. Presence of a gene other than bcl-3 under the control of the bcl-3 promoter suggests that the new gene is a cellular oncogene. This determination can be performed by any means known in the art. Using one means, a bcl-3 promoter probe is hybridized to DNA which is isolated from the neoplastic human blood or bone marrow. If a fragment of different size or composition is found to hybridize to the promoter probe than is found in normal tissue or in germline tissue there is an indication that a gene other than bcl-3 may be under the transcriptional control of the bcl-3 promoter.

Alternatively, amplification of the bcl-3 gene can be accomplished using the polymerase chain reaction, using as template the messenger RNA isolated from the blood or bone marrow cells of a human having a hematopoietic cell neoplasm. One primer to be used in the amplification could be derived from the promoter sequences of bcl-3, the other from the first intron of the myc gene. DNA sequences of the myc oncogene are known, and are available inter alia from the American Type Culture Collection, Rockville, Md. If a fragment is amplified using DNA derived from a malignant source as a template, then there is an indication of a rearrangement of the bcl-3 gene with the myc oncogene. Other means for detecting genes under the control of the bcl-3 promoter known in the art may also be used.

If there is an indication of a bcl-3 rearrangement, the presence of a new gene under the control of the bcl-3 promoter should be confirmed. Cellular oncogenes can be isolated and identified by making DNA clones from DNA of neoplastic cells and isolating those which hybridize to the bcl-3 promoter. Sequences of the cloned DNA fragments which are not derived from the bcl-3 gene could then be used to identify the original location of the putative cellular oncogene and to determine its sequence. Other methods of confirming the presence of a new gene under the control of bcl-3 known in the art could also be used.

According to another method of the present invention, the progress of anti-neoplastic therapy can be monitored or minimal residual disease can be detected. Once again, nucleic acids are isolated from blood or bone marrow cells of a patient with a hematopoietic cell malignancy, wherein there was a rearranged bcl-3 gene in the malignant cells of said patient previously found. Then it is determined whether the rearranged bcl-3 gene found originally in the patient's malignant hematopoietic cells, is present in the nucleic acids of the cells isolated from the patient at the present time. The presence of rearranged bcl-3 genes indicates the continuing presence of malignant cells in the patient.

The patient may be one who is receiving antineoplastic therapy, in which case, therapy could be monitored by determining if there were a decrease in the amount of rearranged bcl-3 genes detectable in the nucleic acids of the patient's hematopoietic cells. Anti-neoplastic therapy would continue until rearranged bcl-3 genes were no longer detectable.

Alternatively, nucleic acids can be isolated from blood or bone marrow cells of a patient whose hematopoietic cell malignancy has been in remission. When rearranged bcl-3 genes are again detectable in the population of nucleic acids isolated from blood or bone marrow cells, there is an indication of recurrence of the malignancy, i.e., minimal residual disease. Once again, the determination of the presence of rearranged bcl-3 genes can be performed either by hybridization of a bcl-3 nucleic acid probe to nucleic acids isolated from the blood or bone marrow cells of the patient or by means of amplification using the polymerase chain reaction and nucleic acid primers. In the case of amplification, primers can be selected which would only amplify a product if rearranged bcl-3 genes were present. Thus one primer could be derived from the bcl-3 promoter or 5' to the promoter, and one primer could be derived from nucleic acid sequences which are not normally adjacent to the bcl-3 promoter, e.g., sequences translocated from another chromosome. Thus, if no amplification product is observed one could conclude that less than about 1 in $10^5$ cells of the blood or bone marrow are malignant. Any other method known in the art for determining the presence of rearranged bcl-3 genes may also be used.

The following are merely exemplary of the invention described above. The invention is not limited to the examples, but is defined by the disclosure and claims which follow.

EXAMPLES

EXAMPLE 1

This example describes the leukemic patient who provided the cells examined in the examples which follow.

We analyzed oncogene rearrangements involving bcl-2 and c-myc in the leukemic specimen of the patient with a very aggressive acute prolymphocytic leukemia (ALL #217) with a t(14;18) translocation and additional cytogenetic abnormalities: 17q+, 12q+, Xp+. The patient had presented with a two-week history of flu-like symptoms, an elevated white blood cell count and a hepatosplenomegaly. The leukemia cells were negative for terminal deoxyribosyltransferase (terminal transferase: TdT) but positive for B-cell-specific markers, and they showed abundant surface immunoglobulin of the IgM and IgD types. Aggressive chemotherapy was started according to standard regimens, but the patient died six weeks after initial diagnosis.

EXAMPLE 2

This example demonstrates that the t(14;18) translocation observed in the patient's leukemic cells in metaphase spreads involved a joining mistake of the bcl-2 gene from chromosome 18 into the immunoglobulin heavy chain locus on chromosome 14.

Figure 1A:
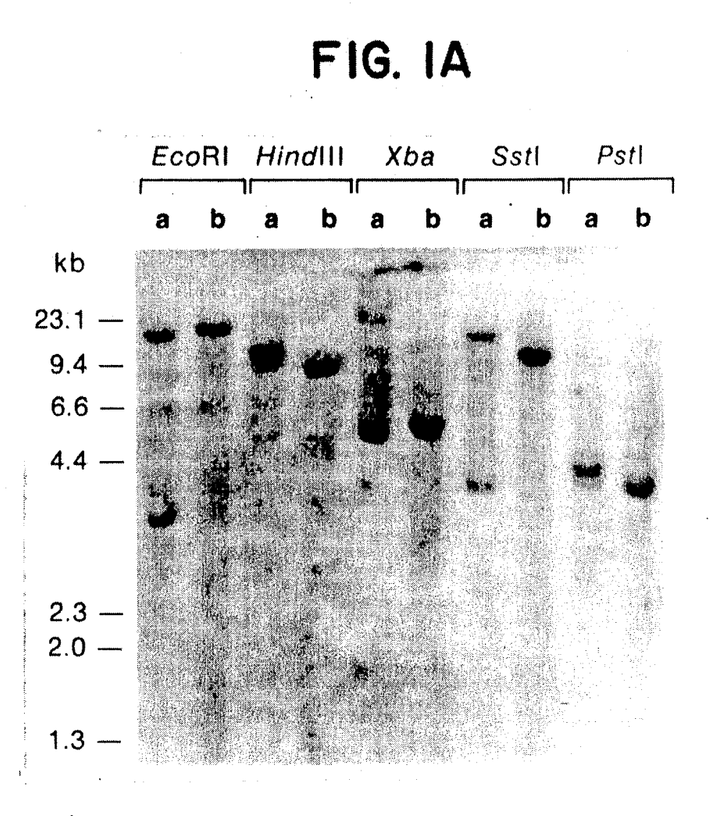
FIG. 1 shows a Southern blot hybridization of the DNA extracted from a patient's acute prolymphocytic leukemia cells (lanes a) and of human placenta DNA (lanes b) used as a germline control to the probe for the joining region ($J_H$) gene of the immunoglobulin heavy chain locus (FIG. 1A) and to the probe for the bcl-2 locus (FIG. 1B) that covers the major breakpoint cluster region of the bcl-2 gene.
Figure 1B:
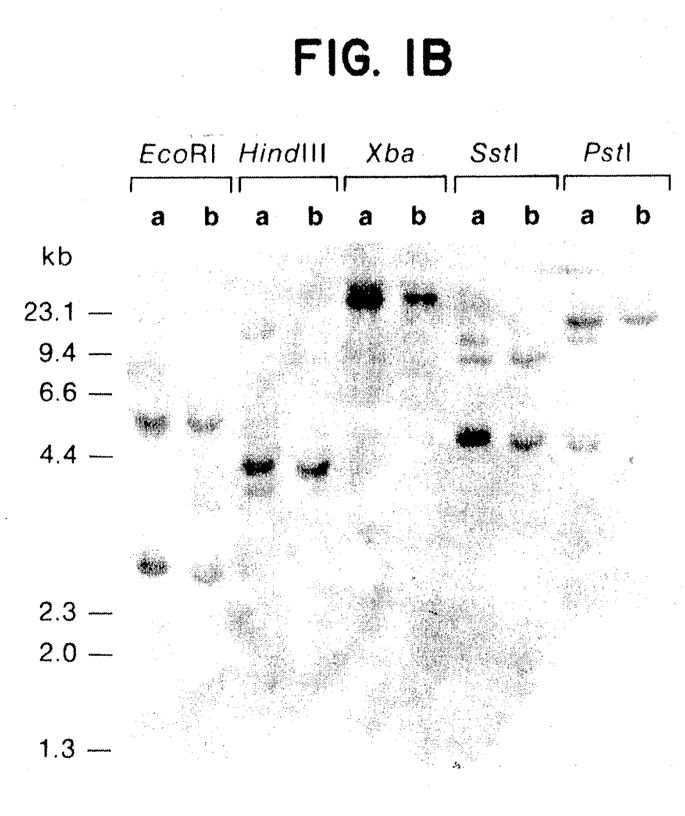

Genomic DNA was prepared from the patient's leukemia cells and analyzed for rearrangement of the bcl-2 gene involved in the t(14;18) translocation. Southern blots of restriction enzyme digested patient DNA were separated on a 0.8% agarose gel and transferred to a nitrocellulose filter after denaturation. The DNA was hybridized to a $^{32}$P-labelled bcl-2 probe that covers the major breakpoint cluster region of the bcl-2 gene and to a $^{32}$P-labelled $J_H$ probe from the immunoglobulin heavy chain joining segment (FIG. 1). Hybridization was carried out in 4×SSC, 2× Denhardt's solution and 50% formamide at 37° C. for 24 hours. Filters were washed at 37° C. in 2×SSC. Blots were exposed for the hours at 70° C. with an intensifying screen.

EXAMPLE 3

This example shows that a c-myc rearrangement was present in the patient's leukemic cells, although not observed cytogenetically.

Figure 2:
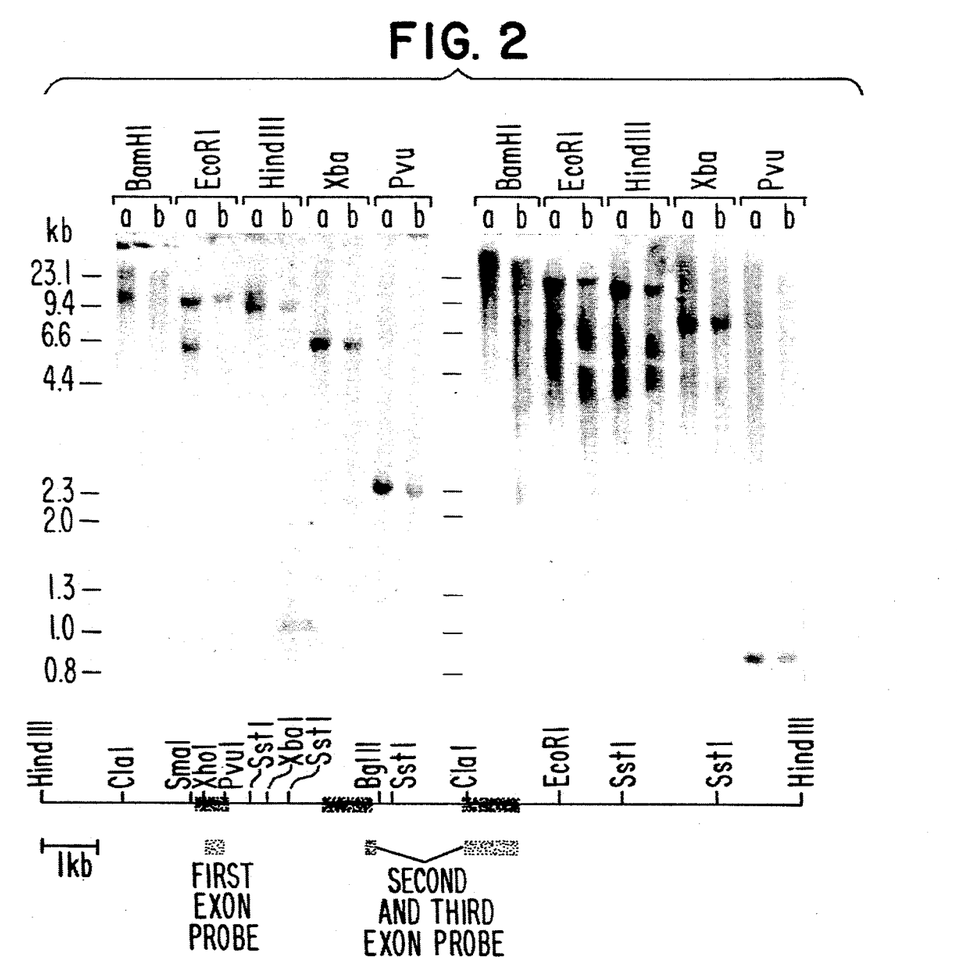
FIG. 2 shows a Southern blot analysis of a patient's DNA and of human placenta DNA by hybridization to the exon 1 probe (right) and 2-3 exon probe (pRyc7.4) (left) of the c-myc gene. A simplified map of the human c-myc gene is shown at the bottom. The exon 1 probe and exon 2-3 probe are indicated.

Because of the highly-aggressive nature of the patient's B-cell disorder, we looked for rearrangement involving c-myc, although both chromosome 8s were cytogenetically normal. Southern blots from Eco-RI-, HindIII-, BamHI- and XbaI-digested DNA were hybridized to two different probes representing the 1 and 2-3 exon probes of c-myc, respectively (FIG. 2). Using the first exon probe (right filter), no rearrangement was detected; however, hybridization to the 2-3 exon probe (left filter) revealed rearrangement of the c-myc gene, which was localized 5' of the c-myc exon 2. We initially thought that this rearrangement was most likely due to a decapitation of the first exon of c-myc, as occurs in sporadic Burkitt lymphoma.

EXAMPLE 4

This example shows the molecular cloning and sequencing of the joining fragment of the truncated c-myc gene and the translocation junction of the bcl-2 gene involved in the t(14;18) translocation.

Figure 3A:
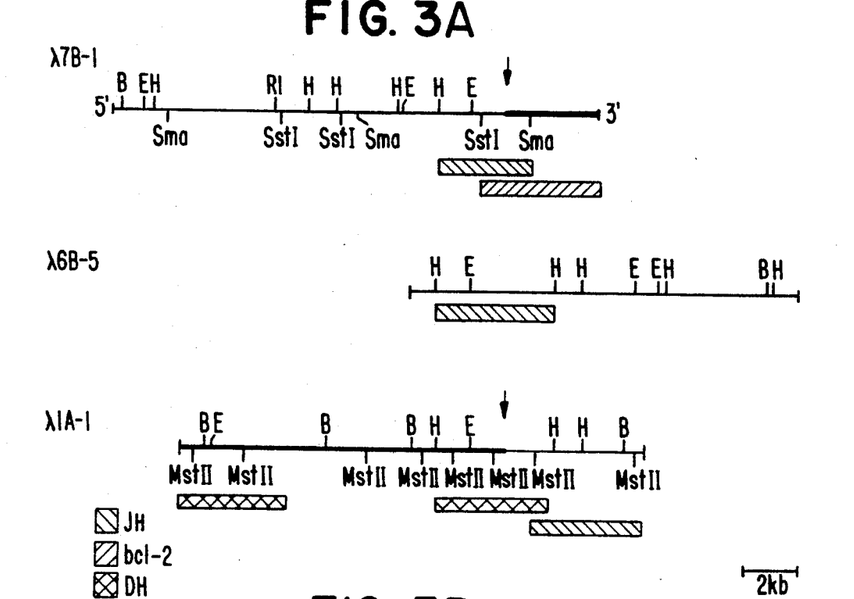
Figure 3B:
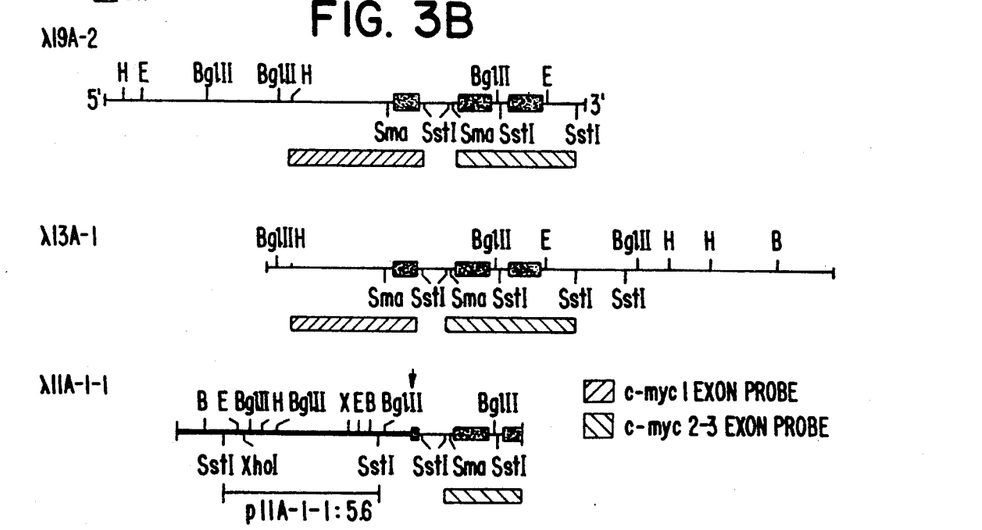
FIG. 3B provides a restriction map of three recombinant clones derived from the genomic library of the patient's DNA hybridizing to the 2-3 exon probe of c-myc. Clones lambda 19A-2 and lambda 13A-1 represent clones containing the normal c-myc gene of chromosomes 8; they also hybridized to the 5' exon probe of c-myc as indicated. Clone lambda 11A-1-1 contains the rearranged c-myc gene. The arrow identifies the breakpoint which occurs in the 3' end of exon of 1 of c-myc, and the bold line shows where the restriction map diverges from the normal chromosome 8. This portion of the clone is derived from chromosome 17.

DNA of the patient's leukemia cells was partially digested with Sau 3A, and DNA fragments with a size of 15-33 kb were collected by sucrose gradient centrifugation. These were ligated with the lambda phage vector EMBLA 3A DNA and packaged in vitro. By screening one million recombinant phage plaques with the 2-3 exon probe of c-myc, the bcl-2 probe and the $J_H$ probe, we obtained 25 independent clones. Six of those were analyzed by restriction enzyme digestion and gene mapping (FIG. 3A and 3B). Clones lambda 7B-1 and lambda 1A-1 (Fig. 3A) represent the rearranged bcl-2 gene involved in the t(14;18) translocation; clone lambda 6B-1 is derived from the germline bcl-2 gene on the normal chromosome 18 and is shown for comparison. Overlapping fragments of clone lambda 7B-1 hybridized to the bcl-2 probe and to the probe specific for the heavy chain joining ($J_H$) segment as shown, indicating that they contain the breakpoint of the t(14;18) translocation on chromosome 14q+. Clone lambda 1A-1 represents the reciprocal of the t(14;18) translocation on chromosome 18q−. Fragments of this clone hybridized to the bcl-2 probe and also to a probe specific for the diversity region ($D_H$) of the immunoglobulin heavy chain locus (Tsujimoto, et al., Science, 1985, 228:1440–1443). The restriction map of the $D_H$ portion of this clone shows similarity to the $D_{H2}$ subunit of the germline diversity region of the immunoglobulin heavy chain gene (Gauwerky, et al., Oncogene 1988, 2:431–435; Tsujimoto, et al., Oncogene 1988, 2:347–351), but there are some alterations. Thus, it appears that the reciprocal of bcl-2 on chromosome 18q− joins into a variant of the $D_{H2}$ segment.

We have also sequenced the fragments involved in the translocation on chromosome 14q+ and chromosome 18q−. The breakpoint occurs in the major breakpoint cluster region (mbcr) of the bcl-2 gene and joins into the J5 segment of the immunoglobulin heavy chain gene on chromosome 14q+, as is common in many follicular lymphomas (Tsujimoto, et al., Science 1984, 226:1097–1099; Tsujimoto, et al., Science 1985, 228:1440–1443; Tsujimoto, et al., Oncogene 1988, 2:347–351; Tsujimoto, et al., Science 1985, 229:1390–1393). Heptamer and nonamer signal sequences on both sides of the breakpoint on chromosome 14q+ and chromosome 18q$^{31}$ are identified, as well as extra nucleotides (N region) that separate the portions of the two joined chromosomes, indicating that this translocation has occurred as a mistake in V-D-J joining at the pre-B-cell stage of B-cell differentiation (Tsujimoto, et al., Science 1985, 229:1390–1393).

FIG. 3B shows the three clones that were obtained from the patient's library using the 2-3 exon probe of c-myc. While clones lambda 19A-2 and lambda 13A-1 revealed a restriction pattern known for the normal c-myc gene, clone lambda 11A-1-1 was found to contain a rearranged c-myc allele. Clone lambda 11A-1-1 hybridized to the 2-3 exon probe, but not to the exon 1 probe of c-myc. Careful analysis showed that the restriction map of the clone lambda 11A-1-1 diverges 5' of an Sst I site in the first intron of c-myc from the normal restriction site of the c-myc gene. Thus, we can assume that a chromosomal break occurred in the c-myc gene very close to the first intron, as is the case in many sporadic Burkitt lymphomas.

EXAMPLE 5

This example demonstrates the localization and characterization of the breakpoint in the c-myc gene.

In order to obtain information on the DNA fragment that joins into the truncated c-myc allele, two subclones designated p 11A-1-1; 5.6 and mp 11A-1-1; 1.7 were obtained. p11A-1-1; 5.6 represents a 5.6 kb SstI-SstI fragment 5' of the breakpoint in pUC19. mp11A-1-1; 1.7 contains a 1.7 kb SstI-SstI fragment that covers the breakpoint in M13. mp11A-1-1; 1.7 was used to localize the breakpoint in c-myc and to characterize the nucleotide sequence surrounding the breakpoint. We found nucleotide sequence homology to c-myc from the 3' region up to the Pvu II site at the end of the first exon of c-myc, and then, exactly in the Pvu II site (FIG. 4), the nucleotide sequence diverges. This is of interest since the c-myc first exon Pvu II site is an area in c-myc where point mutations are known to occur in endemic Burkitt lymphoma cases (Pellici, et al., Proc. Natl. Acad. Sci. USA 1986, 83:2984–2988). The nucleotide sequence 5' of the breakpoint is remarkable in that it contains promoter-like sequences. We identified GC-rich repeats and an Sp1 binding site (Gidoni, et al., Nature 1984, 312:409–413), and there is a CACCC box specific for the major beta globin promoter (Dierks, et al., Cell 1983, 32:695–706) and a stretch of oligonucleotides with 90% homology to the glucocoricoid response element (Payvar et al., Cell 1983, 35:381–392; Bhandari et al., Proc. Natl. Acad. Sci. USA 1988, 85:5789–5793). These sequences are underlied in FIG. 4. Recent work has shown that sequences like these have a strong regulatory potential, and they interact in concert to initiate transcription at a high level (Gidoni et al., Nature 1984, 312:409–413; Dierks et al., Cell 1983, 32:695–706; Payvar et al., Cell 1983, 35:381–392; Bhandari et al., Proc. Natl. Acad. Sci. USA 1988, 85:5789–5793; Schule et al., Nature 1988, 332:87–89; Schule et al., Science 1988, 242:1418–1420; Courey et al., Cell 1988, 55:887–898). Thus, we assumed that the truncated c-myc gene had joined into a strong promoter region of a new gene.

EXAMPLE 6

This example demonstrates the molecular cloning of the bcl-3 gene from human placenta.

We used subclone p11A-1-1; 5.6 as a probe to clone the normal genomic counterpart of the breakpoint region on chromosome 17 from a human placental library. Human placental DNA was partially digested with Sau3A and fractionated over a sucrose gradient. Fragments were used for ligation in lambda phage EMBL3A. The resulting library consisting of 300,000 independent clones was screened with probe p11A-1-1; 5.6 derived from the 5' portion of clone lambda 11A-1-1. Two clones, designated lambda HP2-4 and lambda HP4-4, were carefully analyzed as shown in FIG. 3C. In these clones a 5.0 kb SstI-SstI fragment, p2-4,SS,5.0, was identified that covers the breakpoint and that contains the promoter region of bcl-3, as revealed by hybridization studies.

EXAMPLE 7

This example demonstrates the identification of the chromosome to which bcl-3 maps.

The subclone p11A-1-1; 5.6 was used as a probe for chromosomal localization of the fragment that joins into c-myc, by somatic cell hybrid analysis and chromosomal in situ hybridization. DNA from a panel of well-characterized rodent-human hybrids containing different overlapping subsets of human chromosomes or chromosome regions (Tsai-Pflugfelder et al., Proc. Natl. Acad. Sci. USA 1988, 85:7177–7181) was tested for the presence of sequences homologous to the joining fragment p11A-1-1; 5.6, which was nick translated and used as a probe. Hybrid DNA digested with EcoRI was subjected to analysis onto a Southern blot that was hybridized to probe p11A-1-1; 5.6.

Figure 5:
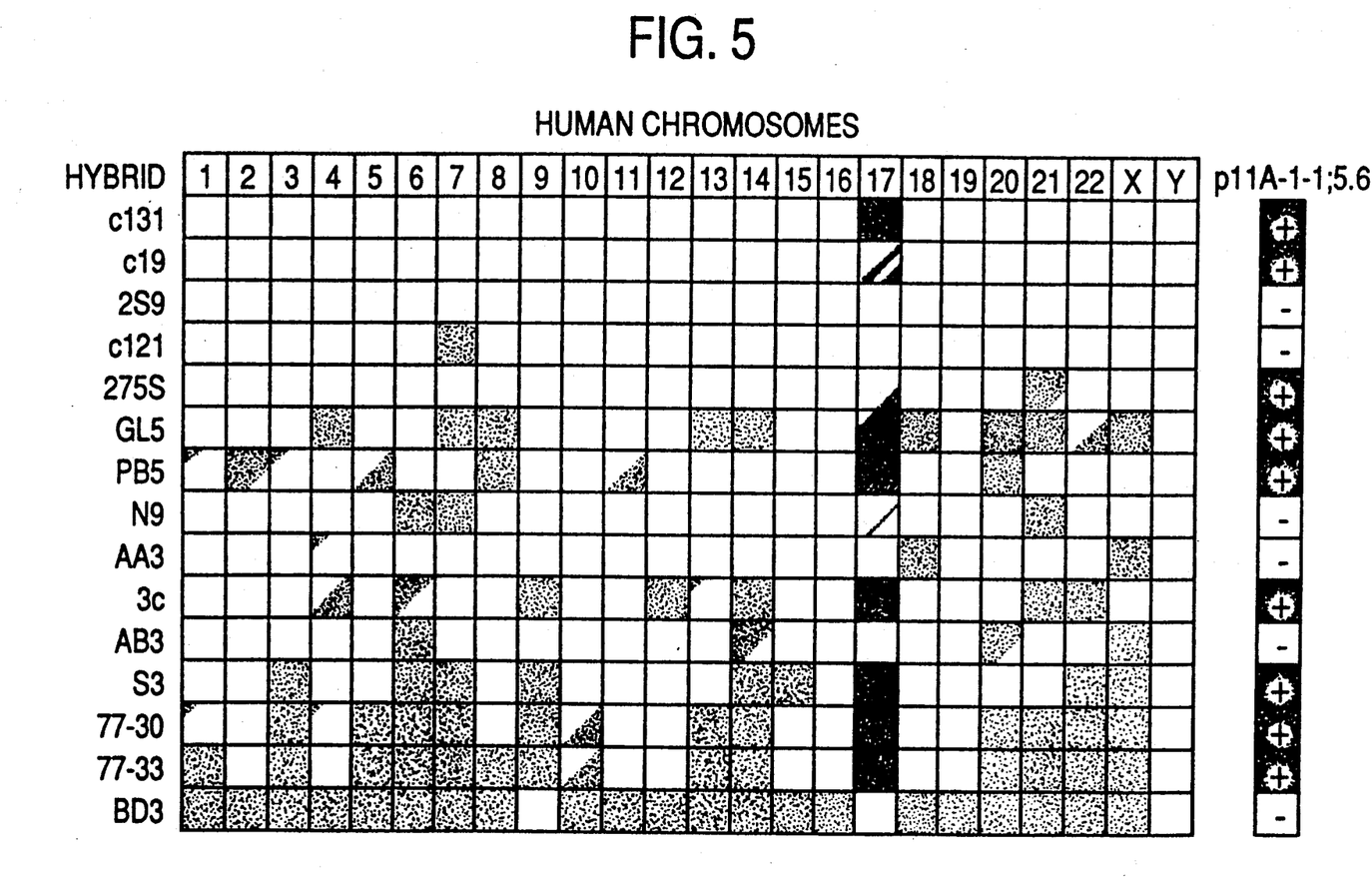

Evaluation of the autoradiogram (not shown) revealed that the locus detected by probe p11A-1-1; 5.6 segregated with a region of the long arm of chromosome 17, as summarized in FIG. 5. Several hybrid cell lines tested retained partial regions of chromosome 17 and thus provided information on the regional localization of the p11A-1-1; 5.6 locus on chromosome 17. The subregions of chromosome 17 retained in these hybrids are defined in Table 1, which illustrates that only hybrids containing chromosome region 17q22 to 17qter retain the locus detected by probe p11A-1-1; 5.6 referred to in Table I. Since the p11A-1-1; 5.6 locus segregates with the PKC alpha locus at 17q22 to 17qter, our locus is distal to Hox-2 (Robertson, Nature 1988, 336:522-524) and thus is distal to the breakpoint characteristic for acute promyelocytic leukemia (APL) (Dayton et al., Proc. Natl. Acad. Sci. USA 1984, 81:4495-4499).

The localization of the c-myc joining fragment to chromosome 17 was confirmed and fine mapped in in situ hybridization of the $^3$H-labelled p11A-1-1; 5.6 probe to metaphase chromosomes of normal human lymphocytes. Metaphase spreads were prepared from normal human male lymphocyte cultures which were stimulated with phytohaemagglutinin for 72 h in vitro. The probe was labeled by nick translation with $^3$H-dTTP (100.1 Ci mmol$^{-1}$; 1 Ci=37GBq;NEN). The techniques used for in situ hybridization were essentially as described by Harper and Saunders (Chromosoma, 1981, vol. 83, pp. 431-439). Chromosome preparations were treated with 100 ug ml$^{-1}$ RNase A (Sigma) in 2×SSC for 20 min at 37° C., then immersed in 70% formamide in 2×SSC, pH 7.0, at 70° C. for 2 min to denature the chromosomal DNA. The chromosomal preparations were then hybridized with $^3$H-labeled p11A-1-1; 5.6 probe (specific activity 3×17$^7$ c.p.m. ml$^{-1}$ in 50% formamide, 2×SSCP (300 mM NaCl, 30 mM sodium citrate, 40 mM NaH$_2$PO$_4$), 1 mg ml$^{-1}$ sonicated salmon sperm DNA, 10% dextran sulfate (Phamacia), pH 7.0, for 20 h at 37° C., rinsed thoroughly in 50% formamide in 2×SSC at 39° C. and then dehydrated in ethanol. Hybridized slides were coated with Kodak NTB2 emulsion (diluted 1:1 with water) and exposed at 4° C. for 16 days. Autoradiographs were developed with Kodak Dektol at 15° C. The chromosomes were then G-banded with a mixture of 6 parts borate buffer (50 mM Na$_2$So$_4$/2.5 mM Na$_2$B$_4$O$_7$, pH 9.2) to 1 part Wright's/Giemsa stain solution.

Figure 6A:
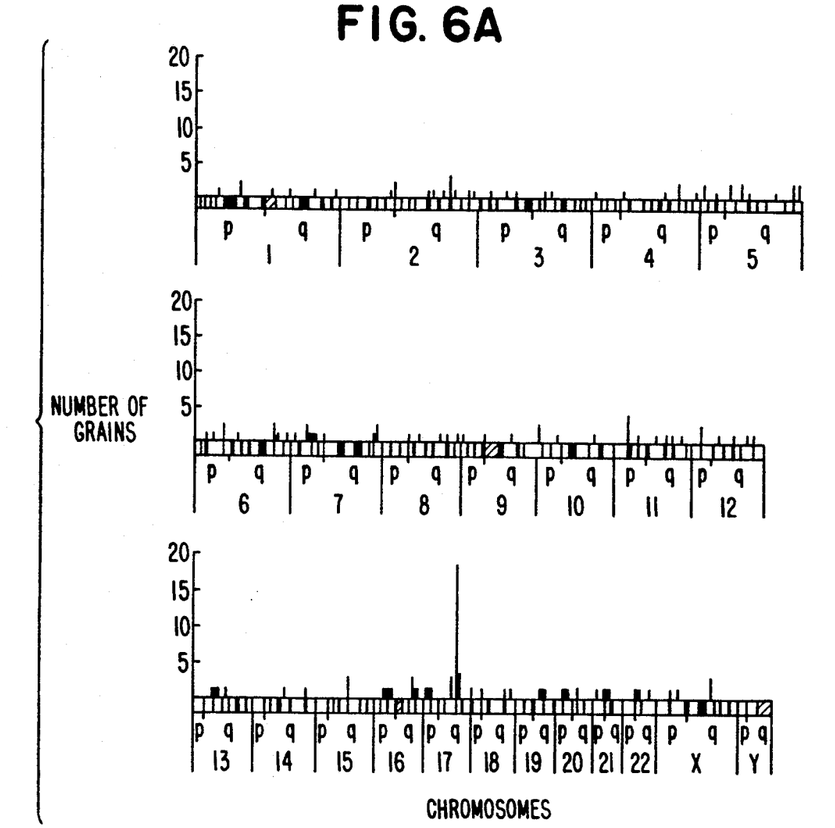
FIG. 6A shows the histogram.
Figure 6B:
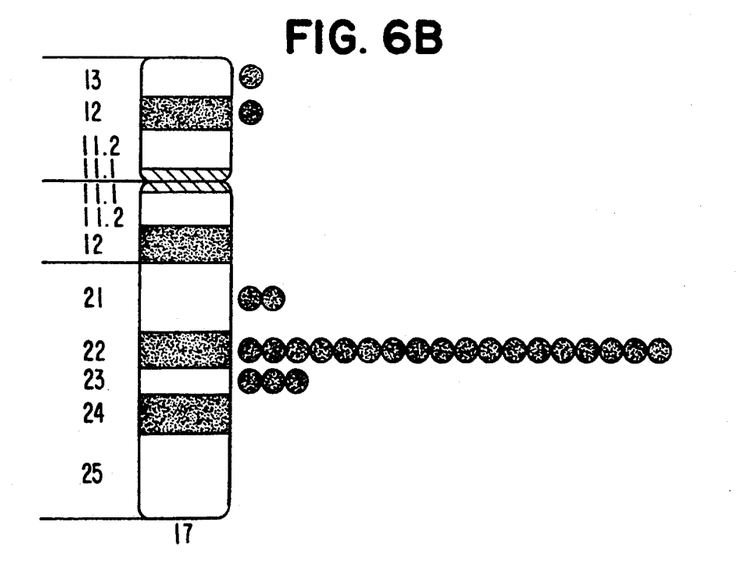
FIG. 6B shows the 23 grains found overlaying 17q21 to 17q23, with the highest peak on 17q22.

After autoradiography, metaphase spreads were analyzed for grain localization. Of the 75 cells examined, 15.8% of the labeling occurred over the distal portion of the long arm of chromosome 17. FIG. 6A shows the histogram. Significant labeling occurred over the middle portion of the long arm of chromosome 17 with the peak of hybridization on 17q22 (FIG. 6B). The long arm of chromosome 17 includes approximately 2.2% of the haploid human genome. Our finding that 15.8% of the hybridization with the p11A-1-1; 5.6 probe localizes to this region of chromosome 17 is highly significant (p' greater than 0.005).

EXAMPLE 8

Since we detected a strong promoter that joined into c-myc in a masked t(18;17) translocation that was undetectable by cytogenetic analysis, we hypothesized that this promoter region might belong to a new gene. Therefore, total cellular RNA was extracted from many different human hematopoietic cell lines representing T-cell, B-cell and myeloid lineages and analyzed on Northern blots (FIG. 7), using as a probe that 5.0 kb SstI-SstI fragment, p2-4,SS,5.0, which covers the break on chromosome 17 and which contains the promoter region (FIG. 3C).

Figure 7A:
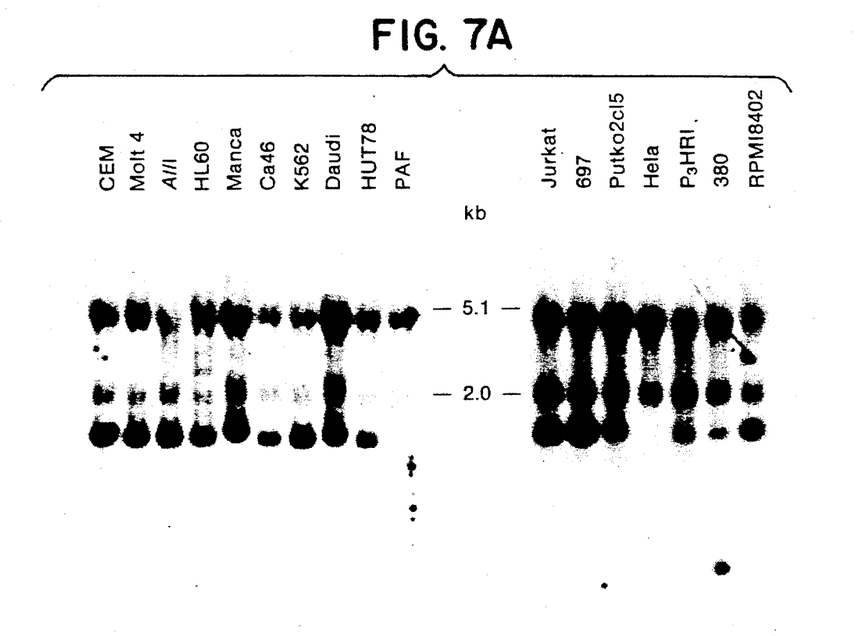
FIG. 7A shows a northern blot analysis of total cellular RNA from different human hematopoietic cell lines, the human SV40 transformed kidney cell line PAF and Hela cells. Total Cellular RNA was extracted and 10 ug of each per lane was analyzed in a 1% formaldehyde agarose gel. After transfer to nitrocellulose filters, the RNA was hybridized to fragment p2-4 4,SS,5.0 that had been nick translated with $^{32}$P. CEM, Molt4, HUT78 and Jurkat represent T-cell leukemia cell lines. Manca, Ca46, Daudi, P$_3$HRI, Putko2c15 are Burkitt lymphoma cell lines, 697 and 380 are pre-B-cell lines; 697 carries a t(1;19), and 380 carries a t(8;14)(14;18) translocation. ALL I is a Ph+ acute lymphoblastic leukemia cell line, and RPMI 8402 is a B-cell line. HL60 is a myeloid leukemia cell line, and K562 is erythroleukemia cell line.

We are able to detect transcripts which had a size of 1.7 kb and which hybridized to the nick-translated p2-4,SS,5.0 probe. FIG. 7A shows that our new gene, which we call bcl-3, was highly expressed in T-cell, B-cell, erythroid, myeloid and monocytic leukemia cell lines but was not expressed in the human SV40 transformed kidney cell line PAF or in Hela cells. We concluded that the fragment p2-4,SS,5.0 contains an exon (or exons) which is transcribed as a 1.7 kb message. Bcl-3 does not appear to be specific for one single hematopoietic cell lineage but rather may be activated at a very early stage of differentiation in hematopoietic cells and maintains expression along the T-cell, B-cell and myeloid lineages.

EXAMPLE 9

This example shows that c-myc is expressed as a truncated RNA transcript in the patient's cells, and that the normal c-myc allele is not expressed. In addition, the bcl-3 transcript is also expressed in these cells.

Figure 7B:
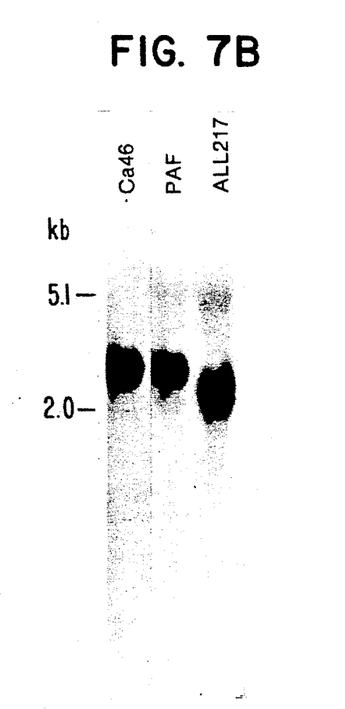
FIG. 7B shows analysis of total cellular RNA extracted from the patient's prolymphocytic leukemia cells (ALL #217). The resulting filter was hybridized to the 2-3 exon probe of c-myc. A transcript of 2.4 kb was detected for the PAF cell line, while the patient's RNA revealed a truncated c-myc transcript of 2.0 kb that is derived from the c-myc gene that is involved in the translocation while the normal c-myc allele is transcriptionally silent.
Figure 7C:
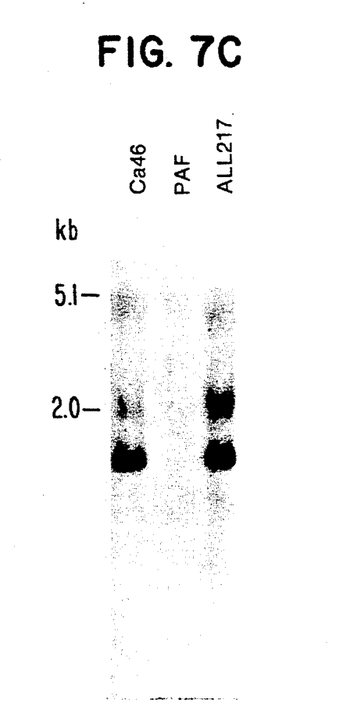
FIG. 7C shows the results when the same filter as in panel B was washed and rehybridized to the nick translated fragment p2-4,SS,5.0. Bcl-3 was found to be expressed as a message of 1.7 kb; PAF did not express bcl-3.

Total cellular RNA from the patient's leukemic cells was subjected to Northern blot analysis and hybridized to the 2-3 exon probe of c-myc. FIG. 7B shows the transcript of the truncated and translocated c-myc gene in the patient's leukemic cells (ALL #217). While a regular c-myc transcript of 2.4 kb was found in PAF cells, the patient's leukemic cells exhibited a highly-expressed 2.0-kb truncated c-myc gene under the influence of the bcl-3 promoter region, as sequencing data previously revealed. Interestingly, the leukemic cells did not express the normal c-myc allele, similar to the case in Burkitt lymphoma where only the translocated myc is transcribed (ar-Rushdi, et al., Science (1983), 222:390-393). The identical filter was then washed and rehybridized to the DNA fragment termed p2-4,SS,5.0. FIG. 7C shows the 1.7 kb band corresponding to the bcl-3 transcript, which is expressed in the patient's leukemic cells but not in human PAF cells.

I claim:

1. A nucleic acid probe of at least 12 nucleotides consisting essentially of a segment of the bcl-3 locus.

2. The nucleic acid probe of claim 1 wherein the segment of the bcl-3 locus is present on a clone selected from the group consisting of: lambda 11A-1-1, lambda HP2-4, and lambda HP4-4.

3. A method of detecting human leukemias, comprising:
   isolating nucleic acids from blood cells or bone marrow cells of a human; and
   determining by hybridization whether in the nucleic acids isolated from said cells a bcl-3 gene is adjacent to sequences different from those to which bcl-3 is adjacent in germline sequences, the presence of different sequences adjacent to bcl-3 indicating a hematopoietic cell neoplasm.

4. The method of claim 3 wherein the step of determining is performed by hybridization of a bcl-3 probe to said nucleic acids which have been digested with a restriction endonuclease and detecting said probe.

5. The method of claim 3 wherein the step of determining is performed by amplification of bcl-3 sequences using nucleic acid primers in a polymerase chain reaction and detecting said amplified sequence.

6. A method of identifying cellular oncogenes, comprising:

isolating nucleic acids from blood or bone marrow cells of humans having a hematopoietic cell neoplasm; and determining by hybridization whether a gene other than bcl-3 is under the transcriptional control of the bcl-3 promoter in the nucleic acids isolated from said cells, a gene other than bcl-3 under the control of the bcl-3 promoter indicating that the gene is a cellular oncogene.

7. The method of claim 6 wherein the step of determining is performed by hybridization of a probe comprising bcl-3 promotor sequences to said nucleic acids which have been digested with a restriction endonuclease and detecting said probe.

8. The method of claim 6 wherein the step of determining is performed by amplification of bcl-3 sequences using nucleic acid primers in a polymerase chain reaction and detecting said amplified sequence.

9. A method of monitoring the progress of anti-neoplastic therapy in a patient having a hematopoietic cell malignancy or of detecting minimal residual disease, comprising:

isolating nucleic acids from blood or bone marrow cells of a patient with a hematopoietic cell malignancy, wherein there is a rearranged bcl-3 gene in malignant cells of said patient; and determining by hybridization whether the rearranged bcl-3 gene is present in the nucleic acids isolated from said blood or bone marrow cells, the presence of rearranged bcl-3 genes indicating the presence of malignant cells in the patient.

10. The method of claim 9 wherein the step of determining is performed by hybridization of a nucleic acid probe comprising bcl-3 sequences to said nucleic acids which have been digested with a restriction endonuclease and detecting said probe.

11. The method of claim 9 wherein the step of determining is performed by amplification of bcl-3 sequences using nucleic acid primers in a polymerase chain reaction and detecting said amplified sequence.

12. The method of claim 9 wherein the patient has received anti-neoplastic therapy.

13. The method of claim 9 wherein the malignancy of said patient has been in remission.

* * * * *